(12) United States Patent
Kitahara et al.

(10) Patent No.: US 6,596,836 B2
(45) Date of Patent: Jul. 22, 2003

(54) POLYISOCYANATE COMPOUNDS, PROCESS FOR PRODUCING THE SAME, AND OPTICAL MATERIALS USING THE SAME

(75) Inventors: Yoshitaka Kitahara, Tokyo (JP); Jian Jiang, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 10/056,020

(22) Filed: Jan. 28, 2002

(65) Prior Publication Data

US 2002/0107353 A1 Aug. 8, 2002

Related U.S. Application Data

(62) Division of application No. 09/362,374, filed on Jul. 28, 1999, now abandoned.

(30) Foreign Application Priority Data

Jul. 29, 1998 (JP) ............................................. 10-213570
Jul. 29, 1998 (JP) ............................................. 10-213571

(51) Int. Cl.⁷ ..................... C08G 18/73; C08G 18/77; C08G 18/52; C08G 18/32; C08G 18/38
(52) U.S. Cl. ............................ 528/44; 528/73; 528/85; 528/76; 252/182.2
(58) Field of Search ............................ 528/44, 73, 85, 528/76; 252/182.2

(56) References Cited

U.S. PATENT DOCUMENTS 5,756,766 A  *  5/1998  Kawauchi et al. ............. 549/22
6,194,603 B1 *  2/2001  Kitahara et al. ............. 560/357
6,313,316 B1 * 11/2001  Kitahara et al. ............. 549/22
6,455,729 B1 *  9/2002  Kitahara et al. ............. 560/357

FOREIGN PATENT DOCUMENTS

| EP | 976728 | * 2/2000 |
|---|---|---|
| JP | 1-295201 | 11/1989 |
| JP | 1-295202 | 11/1989 |
| JP | 2-802 | 1/1990 |
| JP | 2-153302 | 6/1990 |
| JP | 4-159275 | 6/1992 |
| JP | 5-105677 | 4/1993 |
| JP | 6-65193 | 3/1994 |
| JP | 8-208801 | 8/1996 |
| JP | 8-269161 | 10/1996 |
| JP | 8-291210 | 11/1996 |
| JP | 8-291211 | 11/1996 |
| JP | 8-325345 | 12/1996 |
| JP | 9-1565 | 1/1997 |
| JP | 9-71631 | 3/1997 |
| JP | 9-71632 | 3/1997 |
| JP | 10-45707 | 2/1998 |
| JP | 10-245429 | 9/1998 |

OTHER PUBLICATIONS

Database Chemabs 'Online Chemical Abstracts Service, Columbus, Ohio, US STN, Caplus, Accession No. 1994: 508012 XP 002113928 Abstract; RN 156742–88–0, 156742–91–5, 156742–87–9 & JP 06 065193 A (Hoya Corp).

Database Chemabs 'Online Chemical Abstracts Service, Columbus, Ohio, US STN, Caplus, Accession No. 1997: 320993, XP002113929 Abstract; RN 189140–19–0, 189140–20–3, 189140–21–4, 189140–22–5, 189140–18–9 & JP 09 071632 A(Mitsui Toatsu Chemicals Inc).

* cited by examiner

Primary Examiner—Rabon Sergent
(74) Attorney, Agent, or Firm—Morrison & Foerster LLP (57) ABSTRACT

The invention provides a novel polyisocyanate compound which is useful as a starting material for an optical material having a high refractive index, a low dispersion and excellent optical characteristics, and a process for producing this compound at good efficiency. The invention also provides an optical material having a high refractive index, a low dispersion, an excellent transparency without optical distortion and having good solvent resistance and weatherability.

7 Claims, 2 Drawing Sheets

FIG. 1

POLYISOCYANATE COMPOUNDS, PROCESS FOR PRODUCING THE SAME, AND OPTICAL MATERIALS USING THE SAME

This application is based on Japanese patent application Nos. H10-213570 and H10-213571, both filed on Jul. 29, 1998, the entire contents of which are incorporated herein by reference.

FIELD OF THE INVENTION

The invention relates to a polyisocyanate compound and a process for producing the same. In particular, it relates to a novel polyisocyanate compound useful as a starting material for an optical material, and a process for producing the same at good efficiency. It also relates to an optical material and an optical product using the same. Specifically, it relates to an optical material which has excellent optical characteristics such as a high refractive index, a low dispersion, an excellent transparency, lack of optical distortion and the like, and which is also good in solvent resistance and weatherability, and to an optical product formed of this optical material, such as a lens, a prism, optical fibers, a substrate for a recording medium, a filter, a glass, a vase and the like.

BACKGROUND OF THE INVENTION

Recently, plastic materials have been used for optical parts in place of inorganic glass, especially for eyeglass lenses, because they are lightweight and have good dyeability and good impact resistance. In particular, a polyethylene glycol bisallylcarbonate polymer (hereinafter referred to as CR-39) and polymethyl methacrylate (PMMA) have been used, primarily for plastic lenses. However, it has a refractive index of 1.50, which is lower than that of inorganic glass. Therefore, when they are used as lens materials, for example, the thickness of the lenses has to be increased with the increasing power. Consequently, not only is the superiority of plastics as lightweight material been impaired, but also they have not been preferred in view of the aesthetic property. Furthermore, the concave lens, in particular, has had problems when the thickness (edge thickness) of the surrounding portion of the lens is increased causing a birefringence or a chromatic aberration to occur.

For these reasons, in order to be able to decrease the thickness of the lens while applying most of the characteristics of plastics having a low specific gravity, a plastic material having a high refractive index has been in demand. As a material having such a performance, for example, (1) a polymer comprising a xylene diisocyanate compound and a polythiol compound (official gazette of JP-A-63-46213), (2) a resin comprising an aliphatic linear sulfur-containing diisocyanate and a polythiol compound (official gazette of JP-A-2-153302), (3) a polymer comprising a dithian derivative substituted with two isocyanatoalkyl groups and a polythiol (official gazette of JP-A-4-159275) are disclosed.

Although the polymer of item (1) has an increased refractive index by limiting a combination with the polythiol compound to be polymerized, it gives rise to problems that an Abbe number is decreased and a chromatic aberration is increased.

Meanwhile, the resin (2) and the polymer (3) have a high refractive index and the improvement in the chromatic aberration is found therein, but they have a defect that a solvent resistance is poor.

Furthermore, since these prior art polymers are uncrosslinked polymers obtained from bifunctional isocyanate compounds, a special crosslinking agent is needed separately to improve a solvent resistance. Thus, the types of the polythiol compounds that can be polymerized are limited.

SUMMARY OF THE INVENTION

In order to overcome many of the problems in the prior art, the invention provides an optical material having the above-mentioned desirable properties. It is a feature of the invention to provide a novel polyisocyanate compound that can give an optical material having a high refractive index, a low dispersion and an excellent solvent resistance and weatherability, and a process for producing this compound at good efficiency. It is also a feature of the invention to provide an optical material which has excellent optical characteristics such as a high refractive index, a low dispersion, an excellent transparency, lack of optical distortion and the like, and which has good solvent resistance and weatherability, and an optical product formed of this optical material.

In particular, the invention provides a polyisocyanate compound having sulfur atoms, contributing to a high refractive index and a low dispersion, in a main skeleton and having three isocyanates as polymerization functional groups. In addition, the invention provides methods for producing the polyisocyanate compound by an efficient processes. It also provides an optical material formed of a poly(thio)urethane obtained by subjecting a component comprising a polyisocyanate compound and a component comprising a compound having two or more of hydroxyl groups or mercapto or both groups to a polyaddition reaction.

In one aspect, the invention provides a polyisocyanate compound having general formula (I):

(I)

wherein n represents an integer from 1 to 4 and each of the indices n is the same.

In another embodiment, the polyisocyanate compound can be produced by one of the following processes: production process 1, production process 2 and production process 3.

Production process 1 of the invention is a process for producing a polyisocyanate compound represented by general formula (I).

Process 1 comprises:

(a) reacting 1,2,3-trimercaptopropane with a halogenoaliphatic carboxylic acid lower alkyl ester represented by general formula (II)

(II)

wherein X represents a halogen atom, $R^1$ represents a lower alkyl group, and m represents an integer of from 0 to 3, to obtain a tricarboxylic acid ester represented by general formula (III):

(III)

wherein n and $R^1$ are as defined above, (b) converting the tricarboxylic acid ester to a tricarbonyl hydrazide represented by general formula (IV):

(IV)

wherein n is as defined above, and (c) converting the carbonyl hydrazide group into an isocyanate group.

Production process 2 of the invention is a process for producing a polyisocyanate compound represented by general formula (I).

Process 2 comprises:

(a) reacting a 1,2,3-trihalogenopropane with a mercapto-aliphatic carboxylic acid lower alkyl ester represented by general formula (V):

(V)

wherein $R^1$ represents a lower alkyl group, and m represents an integer of from 0 to 3, to obtain a tricarboxylic acid ester represented by general formula (III), (b) converting the tricarboxylic acid ester to tricarbonyl hydrazide represented by general formula (IV):

(IV)

wherein n is as defined above, and (c) converting the carbonyl hydrazide group into an isocyanate group.

Production process 3 of the invention is a process for producing a polyisocyanate compound represented by general formula (I-a):

(I-a)

wherein k represents an integer of from 0 to 2 and each of the indices k is the same.

Process 3 comprises:

(a) reacting 1,2,3-trimercaptopropane with an aliphatic unsaturated carboxylic acid lower alkyl ester represented by general formula (VI):

(VI)

wherein $R^2$ represents a lower alkyl group, and k is as defined above, to obtain a tricarboxylic acid ester represented by general formula (VII):

(VII)

wherein $R^2$ and k are as defined above, (b) converting the tricarboxylic acid ester to tricarbonyl hydrazide represented by general formula (VIII):

(VIII)

wherein k is as defined above, and (c) converting the carbonyl hydrazide group into an isocyanate group.

In another embodiment, the optical material of the invention is formed of a poly(thio)urethane, which is obtained by subjecting a monomer mixture comprising component (A) comprising at least a polyisocyanate compound represented by general formula (I), wherein n represents an integer of from 1 to 4, and component (B) comprising at least one type selected from (a) a compound having two or more mercapto groups in a molecule, (b) a compound having two or more hydroxyl groups in a molecule and (c) a compound having one or more hydroxyl groups and one or more mercapto groups in a molecule to a polyaddition reaction.

The invention is to provide an optical product formed of the above-mentioned optical material.

BRIEF DESCRIPTION OF THE DRAWINGS

The invention will be better understood by reference to the Detailed Description of the Invention when taken together with the drawings, wherein.

DETAILED DESCRIPTION OF THE INVENTION

The polyisocyanate of the invention is a novel compound represented by general formula (I). As is apparent from general formula (I), this novel compound has a structure in which sulfur atoms are bound to the 1-, 2- and 3-positions of propane, respectively, and three isocyanate groups are further provided. Since the sulfur atoms are thus provided in the structure, i.e., the basic skeleton, the refractive index and the Abbe number of the polyisocyanate compound itself are increased. Accordingly, when an optical material is produced using the polyisocyanate compound, the refractive index and the Abbe number of the optical material are also increased. Furthermore, since the polyisocyanate compound has three isocyanate groups, it also works as a crosslinking agent. Accordingly, when the optical material is produced using the polyisocyanate compound, not only a high solvent resistance but also a high heat resistance and excellent mechanical properties can be imparted to the optical material without adding another crosslinking agent as a secondary component. In the polyisocyanate compound, a compound in which n in general formula (I) is 1 or 2 is especially preferable.

When the polyisocyanate compound represented by general formula (I) is used, there is no need to use a crosslinking agent, but a crosslinking agent can also be used conjointly if required.

Examples of the polyisocyanate compound represented by general formula (I) are the following:

The process for producing the polyisocyanate compound represented by general formula (I) may be any process by which a polyisocyanate compound having a desired structure can be produced. However, it can be produced at quite good efficiency according to the processes 1, 2 and 3 of the invention as mentioned below.

Production Process 1

In this production process 1, first, 1,2,3-trimercaptopropane is reacted with a halogeno-aliphatic carboxylic acid lower alkyl ester represented by general formula (II)

$$X-CH_2-(CH_2)_m-COOR^1 \qquad (II)$$

wherein X represents a halogen atom, $R^1$ represents a lower alkyl group, and m represents an integer of from 0 to 3, to form a tricarboxylic acid ester represented by general formula (III):

wherein n is an integer of from 1 to 4, each of the indices n is the same and $R^1$ is as defined above.

In this reaction, it is preferable that 1 mol of 1,2,3-trimercaptopropane is reacted with substantially 3 moles of the halogeno-aliphatic carboxylic acid lower alkyl ester represented by general formula (II) in the presence of a hydrogen halide trapping agent. In this case, an appropriate solvent can be used as required.

The tricarboxylic acid ester represented by general formula (III) is reacted with hydrazine monohydrate or the like to lead the same to a tricarbonyl hydrazide represented by general formula (IV):

wherein n is as defined above. At this time, a solvent such as a lower alcohol or the like can be used as required.

Finally, the tricarbonyl hydrazide represented by general formula (IV) is reacted with nitrous acid in, for example, a hydrochloric acid aqueous solution to form carbonyl azide, and the heat transfer is conducted to convert a carbonyl azide group into an isocyanate group, whereby a desired polyisocyanate compound represented by general formula (I):

wherein n is as defined above, is obtained.

Production Process 2

In this production process 2, first, the 1,2,3-trihalogenopropane is reacted with a mercapto-aliphatic carboxylic acid lower alkyl ester represented by general formula (V)

$$HS-CH_2-(CH_2)_m-COOR^1 \qquad (V)$$

wherein $R^1$ represents a lower alkyl group, and m represents an integer of from 0 to 3, to obtain a tricarboxylic acid ester represented by general formula (III):

wherein n and $R^1$ are as defined above.

In this reaction, it is preferable that 1 mol of the 1,2,3-trihalogenopropane is reacted with substantially 3 moles of the mercapto-aliphatic carboxylic acid lower alkyl ester represented by general formula (V) in the presence of a hydrogen halide trapping agent. In this case, an appropriate solvent can be used as required.

Subsequently, the tricarboxylic acid ester represented by general formula (III) is, as in the above-mentioned production process 1, led to a carbonyl hydrazide, and a carbonyl hydrazide group is then converted into an isocyanate group to obtain a desired polyisocyanate compound represented by general formula (I).

Production Process 3

The production process 3 is a process for producing a polyisocyanate compound in which n in general formula (I) is between 2 and 4.

In this production process 3, first, 1,2,3-trimercaptopropane is reacted with an aliphatic unsaturated carboxylic acid lower alkyl ester represented by general formula (VI):

$$CH_2=CH-(CH_2)_k-COOR^2 \qquad (VI)$$

wherein $R^2$ represents a lower alkyl group, and k represents an integer of from 0 to 2, to obtain a tricarboxylic acid ester represented by general formula (VII):

(VII)

wherein R² and k are as defined above.

In this reaction, it is preferable that 1 mol of 1,2,3-trimercaptopropane is reacted with substantially 3 moles of the aliphatic unsaturated carboxylic acid lower alkyl ester represented by general formula (VI) in the presence of a radical or anionic catalyst. In this case, an appropriate solvent can be used as required.

Subsequently, the tricarboxylic acid ester represented by general formula (VII) is reacted with hydrazine monohydrate or the like to lead the same to a tricarbonyl hydrazide represented by general formula (VIII):

(VIII)

wherein k is as defined above. In this case, a solvent such as a lower alcohol can be used as required.

Finally, the tricarbonyl hydrazide represented by general formula (VIII) is reacted with nitrous acid in, for example, a hydrochloric acid aqueous solution to form carbonyl azide, and the heat transfer is conducted to convert a carbonyl azide group into an isocyanate group, whereby a desired polyisocyanate compound represented by general formula (I-a):

(I-a)

wherein k is as defined above, is obtained.

Incidentally, the lower alkyl group indicated at $R^1$ and $R^2$ is a methyl group, an ethyl group, an n-propyl group, an isopropyl group or the like.

The polyisocyanate compound represented by general formula (I) can also be produced by a phosgene method other than the above-mentioned processes of the invention.

The phosgene method is described by taking an example. First, 1 mol of the 1,2,3-trimercaptopropane is reacted with substantially 3 moles of a halogenoacetonitrile in the presence of a hydrogen halide trapping agent to obtain 1,2,3-tris(cyanomethylthio)propane represented by formula (IX):

(IX)

Then, the compound represented by general formula (IX) is subjected to hydrogenation to lead it to 1,2,3-tris(aminoethylthio)propane represented by general formula (X):

(X)

Then, the compound represented by general formula (X) is reacted with phosgene to obtain desired 1,2,3-tris(isocyanatoethylthio)propane represented by formula (I-b):

(I-b)

Component (A) may contain, to appropriately improve properties and the like of the optical material, one or two or more types of a compound having two or more isocyanate groups in a molecule other than the polyisocyanate compound represented by the above-mentioned general formula (I). Specific examples of these compounds include o-xylene diisocyanate, m-xylene diisocyanate, p-xylene diisocyanate, α,α,α',α'-tetramethyl-p-xylene diisocyanate, α,α,α',α'-tetramethyl-m-xylene diisocyanate, 1,3,5-tris(isocyanatomethyl)benzene, hexamethylene diisocyanate, 1,4-diisocyanatobutane, isophorone diisocyanate, norbornene diisocyanate, bis(4,4'-isocyanatocyclohexyl)methane, 1,3-bis(isocyanatomethyl)cyclohexane, 1,3,5-tris(isocyanatomethyl)cyclohexane, 1,4-diisocyanatocyclohexane, 1,3,5-triisocyanatocyclohexane, lysine triisocyanate, 2,5-bis(isocyanatomethyl)-1,4-dithian, 1,3-dithiolan-4,5-diisocyanate, 4,5-bis(isocyanatomethyl)-1,3-dithiolan, isocyanatomethyl sulfide, 2-isocyanatoethyl sulfide, bis(isocyanatomethylthio)methane, 1,2-bis(isocyanatomethylthio)ethane, bis(2-isocyanatoethylthio)methane, 1,2-bis(2-isocyanatoethylthio)ethane, 1,7-diisocyanato-2,4,6-trithiaheptane, 1,5-diisocyanato-2-isocyanatomethyl-3-thiapentane, 1,4-diisocyanato-2-isocyanatomethyl-3-thiabutane and the like.

The content of the polyisocyanate compound represented by general formula (I) in the component (A) is preferably 0.1 mol % or more, especially preferably 5 mol % or more.

Component (B), another starting material of the poly(thio)urethane, a component comprising at least one type selected from (a) a compound having two or more mercapto groups in a molecule, (b) a compound having two or more hydroxyl groups in a molecule and (c) a compound having one or more hydroxyl groups and one or more mercapto groups in a molecule is used.

Examples of the compound having two or more mercapto groups in a molecule as the component (a) here include 2,5-bis(mercaptomethyl)-1,4-dithian, 2,5-bis(mercaptomethyl)-1,4-dithian dimer and polymer (trimer or higher polymer), 1,2,3-trimercaptopropane, tetrakis(7-mercapto-2,5-dithiaheptyl)methane, 1,2-ethanedithiol, 1,3-propanedithiol, tetrakismercaptomethylmethane, 2-mercaptoethyl sulfide, pentaerythritol tetrakismercaptopropionate, pentaerythritol tetrakismercaptoacetate, 1,2-benzenedithiol, 1,3-benzenedithiol, 1,4-benzenedithiol, 1,3,5-benzenetrithiol, 1,2-dimercaptomethylbenzene, 1,3-dimercaptomethylbenzene, 1,4-dimercaptomethylbenzene, 1,3,5-trimercaptomethylbenzene, toluene-3,4-dithiol, tris(3-mercaptopropyl)isocyanurate, 1,3-bis(mercaptomethyl) cyclohexane, 1,4-bis(mercaptomethyl)cyclohexane, 2,2-bis (mercaptomethyl)-1,3-propanedithiol, 1,2-bis(2-mercaptoethylthio)-3-mercaptopropane, 4,8-bis (mercaptomethyl)-3,6,9-trithia-1,11-undecanedithiol and the like.

Examples of the compound having two or more hydroxyl groups in a molecule as the component (b) include ethylene glycol, trimethylolpropane, glycerin, dihydroxybenzene, catechol, 4,4'-dihydroxyphenyl sulfide, 2-hydroxyethyl sulfide, bisphenol A.propylene oxide 5-mol adduct, glycerin-propylene oxide 3-mol adduct and the like.

Examples of the compound having one or more hydroxyl groups and one or more mercapto groups in a molecule as the component (c) include 2-mercaptoethanol, 2,3-dimercaptopropanol, 1,2-dihydroxy-3-mercaptopropane, 4-mercaptophenol and the like.

As component (B), a mercapto group-containing compound is preferable. Especially, 2,5-bis(mercaptomethyl)-1,4-dithian and its oligomer represented by general formula (II-a):

wherein p is an integer of from 1 to 20, and oligomers thereof are preferable.

With respect to the ratio of the component (A) to the component (B) in the invention, it is preferable that the molar ratio of the isocyanate group in the component (A) to the total amount of the mercapto group and the hydroxyl group in the component (B), NCO group/(SH group+OH group), is in the range of from 0.95 to 1.05.

The monomer mixture comprising the component (A) and the component (B) may contain one or two or more types of the compound having two or more vinyl groups in the molecule to appropriately improve the properties and the like of the optical material in addition to the components (A) and (B). With respect to the ratio of these compounds used at this time, it is preferable that the (isocyanate group+vinyl group)/(mercapto group+hydroxyl group) molar ratio is in the range of from 0.95 to 1.5 and the (vinyl group)/ (isocyanate group) molar ratio is 0.7 or less, and that polymerizable functional groups contained in the component (B) are all mercapto groups. Specific examples of these compounds include 2,5-bis(2-thia-3-butenyl)-1,4-dithian, divinylbenzene, ethylene glycol di(meth)acrylate, polyethylene glycol di(meth)acrylate, a urethane-modified (meth) acrylate comprising at least two (meth)acryloxy groups in a molecule and the like. By the way, the above-mentioned (meth)acrylate means both of an acrylate and a methacrylate, and the (meth)acryloxy group means both of an acryloxy group and a methacryloxy group.

To the optical material of the invention can be added an ultraviolet absorber, a coloring matter, a pigment and the like for improving light absorption characteristics, an antioxidant, a coloration inhibitor and the like for improving a weatherability, and a release agent and the like for improving a moldability, as required.

Examples of the ultraviolet absorber include a benzotriazole type, a benzophenone type, a salicylic acid type and the like. Examples of the coloring matter and the pigment include an anthraquinone type, an azo type and the like.

Examples of the antioxidant and the coloration inhibitor include a monophenol type, a bisphenol type, a high-molecular phenol type, a sulfur type, a phosphorus type and the like. Examples of the release agent include a fluorine-type surfactant, a silicone-type surfactant, an acidic phosphate, a higher fatty acid and the like.

A catalyst may be used, as required, to improve polymerization. For example, an amine compound, an organic metal compound and the like are effective. Specific examples thereof include triethylenediamine, hexamethylenetetramine, N,N-dimethyloctylamine, N,N,N', N'-tetramethyl-1,6-diaminohexane, 4,4'-trimethylenebis(1-methylpiperidine), 1,8-diazabicyclo-(5,4,0)-7-undecene, dimethyltin dichloride, dimethyltin bis (isooctylthioglycolate), dibutyltin dichloride, dibutyltin dilaurate, dibutyltin maleate, dibutyltin maleate polymer, dibutyltin diricinoleate, dibutyltin bis(dodecylmercaptide), dibutyltin bis(isooctylthioglycolate), dioctyltin dichloride, dioctyltin maleate, dioctyltin maleate polymer, dioctyltin bis(butylmaleate), dioctyltin dilaurate, dioctyltin diricinoleate, dioctyltin dioleate, dioctyltin di(6-hydroxy) caproate, dioctyltin bis(isooctylthioglycokate), didodecyltin diricinoleate, copper oleate, copper acetylacetonate, iron acetylacetonate, iron naphthenate, iron lactate, iron citrate, iron gluconate, potassium octanate, 2-ethylhexyl titanate and the like. The above-mentioned catalysts are effectively used either singly or in combination of two or more types.

When a vinyl compound is contained in the monomer mixture, the use of an organic peroxide, an azo compound or the like other than the above-mentioned catalyst is also effective.

An optical material using the polyisocyanate compound of the invention can be produced. The following is but one example.

A uniform mixture of the component (A), the component (B), the additives and the catalyst is subjected to a known cast polymerization method. That is, it is cast into a die which is a combination of a glass or metal mold and a gasket made of a resin, and cured by heating. In order to expedite withdrawal of the resin after molding, the mold may previously be subjected to release agent treatment, or a release agent may be added to the mixture of the component (A), the component (B) and the like. The polymerization temperature varies depending on the compound used. It is usually between −20 and +150° C. The polymerization time is between 0.5 and 72 hours. The optical material of the invention can easily be dyed in water or an organic solvent using an ordinary disperse dye. At this time, for further expediting the dyeing, a carrier may be added or heating may be conducted. The optical material is used as a plastic lens especially preferably, but is not limited thereto.

EXAMPLES

The invention is illustrated more specifically by referring to the following Examples. However, the invention is not intended to be limited to these Examples.

The properties of the polyisocyanate compounds and optical materials (polymers) were evaluated according to the following methods:

(1) $^1$H-NMR spectrum (proton nuclear magnetic resonance spectrum): Measured using an FT-NMR Device EX 270 Model supplied by JEOL.

(2) IR spectrum (infrared absorption spectrum): Measured using a MAGNA-IR Spectrometer 560 Model supplied by Nicolet.

(3) Refractive index ($n_D$) and Abbe number ($v_D$): Measured at 20° C. using a precision refractometer KPR-200 Model supplied by Kalnew.

(4) Appearance: Visually observed.

(5) Weatherability: A lens (optical product using an optical material) was mounted on a weather meter fitted with a sunshine carbon arc lamp. When 200 hours passed, the lens was taken out, and the color thereof was compared with that of the lens before the test. The weatherability was evaluated according to the following standard.

○: unchanged

Δ: slightly yellowed

×: yellowed (6) Solvent resistance: A wiping test using acetone was conducted, and the solvent resistance was evaluated according to the following standard.

○: unchanged

×: The surface is roughened or swollen.

(7) Optical distortion: Visually observed by the Schlieren method. The optical distortion was evaluated according to the following standard.

○: No distortion is observed.

×: Distortion is observed.

Example 1

Production of 1,2,3-tris(isocyanatoethylthio)propane 1,2,3-Trismercaptopropane (28.0 g, 0.20 moles) and 51.7 g (0.6 moles) of methyl acrylate were dissolved in 300 ml of chloroform. Triton B (40% by weight methanol solution, 0.6 g) was added as a catalyst in an ice bath, and the solution was stirred under reflux for 3 hours. The reaction solution was allowed to cool, then washed with a dilute sodium hydroxide aqueous solution and with water in this order, and dried over magnesium sulfate. Thereafter, chloroform was fully removed to obtain 71.5 g (0.18 moles) of colorless transparent 1,2,3-tris(methyloxycarbonylethylthio)propane.

The ester compound was dissolved in 50 ml of methanol, and added dropwise to a mixed solution of 81.0 g (1.62 moles) of hydrazine monohydrate and 90 ml of methanol at room temperature. After the completion of the dropwise addition, the mixture was stirred at 70° C. for 4 hours. After the mixture was allowed to cool, white crystals precipitated were collected through filtration, and recrystallized from methanol-water to obtain 69.4 g (0.17 moles) of 1,2,3-tris(hydrazinocarbonylethylthio)propane.

Figure 1:
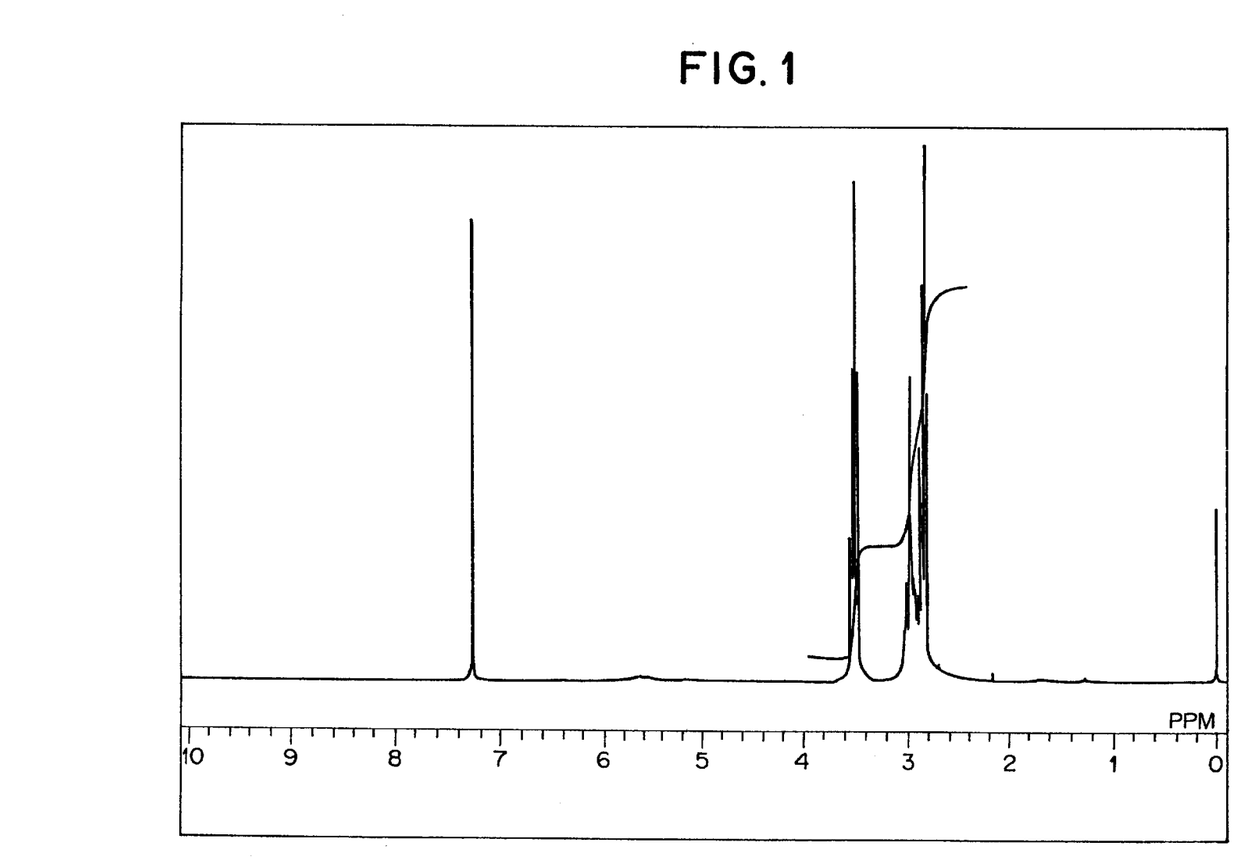
FIG. 1 shows an $^1$H-NMR spectrum of 1,2,3-tris (isocyanatoethylthio)propane obtained in Production Example 1.
Figure 2:
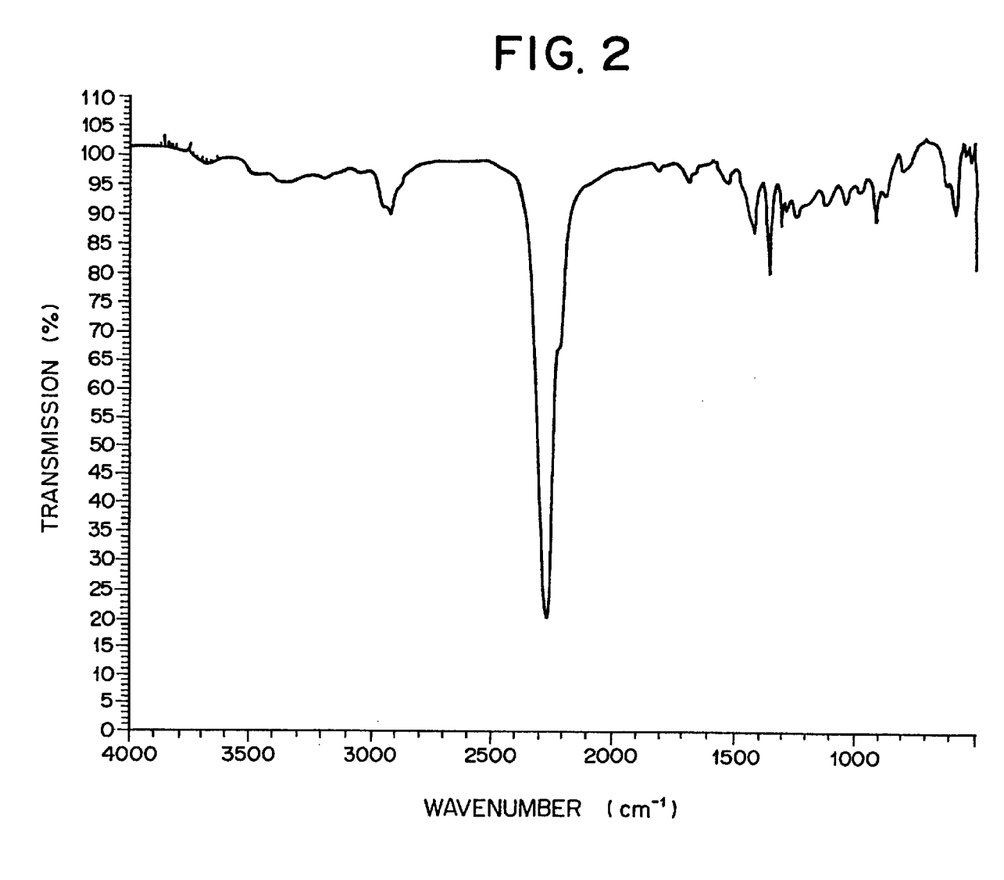
FIG. 2 shows an IR spectrum of 1,2,3-tris (isocyanatoethylthio)propane obtained in Production Example 1.

The hydrazide compound was dissolved in 280 g of a 7.2% by weight hydrochloric acid aqueous solution, and 36.1 g (0.52 moles) of sodium nitrite were added to a suspension with 160 ml of toluene. After the completion of the addition, the stirring was continued for 1 hour. The organic phase was extracted from the suspension, washed with water, dried (magnesium sulfate), and then heated to complete the transition reaction. Toluene as a solvent was fully removed from the reaction solution to obtain 46.0 g (0.13 moles) of a colorless transparent reaction product. This reaction product was identified to be a desired polyisocyanate compound from the $^1$H-NMR spectrum and the IR spectrum. The $^1$H-NMR spectrum of this novel polyisocyanate compound is shown in FIG. 1, and the IR spectrum thereof in FIG. 2.

Application Example 1

A mixture of 0.08 moles of 1,2,3-tris(isocyanatoethylthio) propane (designated SP-1 in Table 1) obtained in Example 1, 0.12 moles of 2,5-bis(mercaptomethyl)-1,4-dithian dimer (designated DBMD in Table 1) and $1.2 \times 10^{-4}$ moles of dibutyltin dilaurate (designated DBTDL in Table 1) was uniformly stirred, and cast into glass molds for forming a lens. The mixture was polymerized at 50° C. for 10 hours, then at 60° C. for 5 hours and further at 120° C. for 3 hours to obtain a plastic lens. The properties of the resulting plastic lens are shown in Table 1. From Table 1, it was found that the polymer obtained by using the polyisocyanate compound of Example 1 was colorless and transparent, the refractive index ($n_D$) was as high as 1.69, the Abbe number ($v_D$) was also as high as 36 (low dispersion), the weatherability and the solvent resistance were excellent, and no optical distortion was observed.

Application Examples 2 to 6

The same procedure as in Application Example 1 was conducted except using a monomer composition comprising the polyisocyanate compound SP-1 [1,2,3-tris(isocyanatoethylthio)propane] obtained in Example 1 or 1,2,3-tris(isocyanatomethylthio)propane (designated SP-2 in Table 1) as shown in Table 1 to obtain a plastic lens. The properties of these plastic lenses were shown in Table 1. From Table 1, it was found that the resulting plastic lenses were colorless and transparent, the refractive index ($n_D$) was as high as between 1.65 and 1.70, the Abbe number ($v_D$) was also as high as between 34 and 39 (low dispersion), the weatherability and the solvent resistance were excellent, and no optical distortion was observed.

Application Comparative Example 1

A mixture of 0.06 moles of pentaerythritol tetrakismercaptopropionate (designated PETMP in Table 1), 0.12 moles of m-xylene diisocyanate (designated XDI in Table 1) and $1.2 \times 10^{-4}$ moles of dibutyltin dilaurate (designated DBTDL in Table 1) was uniformly stirred, and cast into glass molds for forming a lens. The mixture was polymerized at 50° C. for 10 hours, then at 60° C. for 5 hours and further at 120° C. for 3 hours to obtain a plastic lens. The properties of the resulting plastic lens are shown in Table 1. From Table 1, it was found that the plastic lens in Application Comparative Example 1 was colorless and transparent, no optical distortion was observed, and the solvent resistance was excellent, but the refractive index was as low as 1.59.

Application Comparative Examples 2 and 3

The same procedure as in Application Comparative Example 1 was conducted except using monomer compositions shown in Table 1 to obtain plastic lenses. The properties of these plastic lenses were shown in Table 1. From Table 1, it was found that the plastic lens in Application Comparative Example 2 had a high refractive index of 1.68 and was excellent in the solvent resistance. However, it was colored yellow, the Abbe number was as low as 25, the weatherability was poor, and the optical distortion was observed. Further, the plastic lens in Application Comparative Example 3 was colorless and transparent, the refractive index was as high as 1.68, and no optical distortion was observed. However, the Abbe number was as low as 29, and the solvent resistance was also poor.

TABLE 1

|  |  | Component (A) (mol) | Component (B) (mol) | Catalyst (mol) | $n_D/v_D$ | Appearance | Weatherability | Solvent resistance | Optical distortion |
|---|---|---|---|---|---|---|---|---|---|
| Application Example | 1 | SP-1 (0.08) | DBMD (0.12) | DBTDL ($1.2 \times 10^{-4}$) | 1.69/36 | colorless, transparent | ○ | ○ | ○ |
|  | 2 | SP-1 (0.04) IPDI (0.06) | BMMD (0.12) | DBTDC ($1.2 \times 10^{-4}$) | 1.65/39 | colorless, transparent | ○ | ○ | ○ |
|  | 3 | SP-1 (0.10) | TMP (0.10) | DBTDL ($1.5 \times 10^{-4}$) | 1.66/37 | colorless, transparent | ○ | ○ | ○ |
|  | 4 | SP-2 (0.08) | BMMD (0.12) | DMTDC ($1.2 \times 10^{-4}$) | 1.67/36 | colorless, transparent | ○ | ○ | ○ |
|  | 5 | SP-2 (0.10) | BMMC (0.06) TMP (0.06) | DBTDL ($1.5 \times 10^{-4}$) | 1.66/39 | colorless, transparent | ○ | ○ | ○ |
|  | 6 | SP-2 (0.04) IMTM (0.06) | DBMD (0.12) | DMTDC ($1.2 \times 10^{-4}$) | 1.70/34 | colorless, transparent | ○ | ○ | ○ |
| Application Comparative Example | 1 | XDI (0.12) | PETMP (0.06) | DBTDL ($1.2 \times 10^{-4}$) | 1.59/35 | colorless, transparent | Δ | ○ | ○ |
|  | 2 | TDI (0.12) | XDT (0.07) PETMA (0.025) | DBTDL ($1.2 \times 10^{-4}$) | 1.68/25 | yellow | × | ○ | × |
|  | 3 | TPDI (0.10) | XDT (0.10) | DBTDL ($1.0 \times 10^{-4}$) | 1.68/29 | colorless, transparent | Δ | × | ○ |

Note:
SP-1: 1,2,3-tris(isocyanatoethylthio)propane,
SP-2: 1,2,3-tris(isocyanatomethylthio)propane,
IPDI: isophorone diisocyanate,
IMTM: bis(isocyanatomethylthio)methane,
DBMD: 2,5-bis(mercaptomethyl)-1,4-dithian dimer,
BMMD: 2,5-bis(mercaptomethyl)-1,4-dithian,
BMMC: 2,5-bis(mercaptomethyl)cyclohexane,,
TMP: 1,2,3-trimercaptopropane,
DBTDL: di-n-butyltin dilaurate,
DMTDL: dimethyl tin-dichloride,
DBTDC: di-n-butyltin dichloride,
XDI: m-xylene diisocyanate,
TDI: tolylene diisocyanate,
TPDI: 2,4-dithiapentane-1,3-diisocyanate
PETMP: pentaerythritol tetrakis(3-mercaptopropionate),
XDT: m-xylene dithiol,
PETMA: pentaerythritol tetrakis(2-mercaptoacetate)

The invention provides a polyisocyanate compound having a aliphatic chain comprising sulfur atoms as a basic skeleton, in which the refractive index and the Abbe number are high. It has three isocyanate groups, and is easily polymerized with at least one type of a compound having two or more hydroxyl groups in a molecule, a compound having two or more mercapto groups in a molecule and a compound having one or more hydroxyl groups and one or more mercapto groups in a molecule to provide a three-dimensionally crosslinked optical material. Since the optical material obtained by using this polyisocyanate compound contains the sulfur atoms in the main chain and is further crosslinked, the refractive index and the Abbe number are high, the weatherability, the solvent resistance and the transparency are excellent, and no optical distortion is observed. The optical material is preferably used in optical products, for example, lenses such as a spectacle lens, a camera lens and the like, a prism, optical fibers, substrates for recording medium used in an optical disk, a magnetic disk and the like, a filter and the like. It can also be used in ornamental products such as a glass, a vase and the like which are obtained by making the most of the property of the high refractive index.

The descriptions presented herein enable a person of ordinary skill in the art to make and use the invention. Although the invention has been fully described by way of examples with reference to the accompanying drawings, it is to be noted that various modifications will be readily apparent to those skilled in the art, and the generic principles defined herein may be applied to other embodiments and applications without departing from the spirit and scope of the invention. Thus, the invention is not intended to be limited to the embodiments shown, but is to be accorded the widest scope consistent with the principles and features disclosed herein.

What is claimed is:

1. A monomer mixture, comprising:

component (A) comprising at least a polyisocyanate compound represented by general formula (I):

(I)

wherein n represents an integer of from 1 to 4 and each of the indices n is the same, and component (B) comprising at least one compound selected from the group consisting of (a) a compound having two or more mercapto groups in a molecule, (b) a compound having two or more hydroxyl groups in a molecule and (c) a compound having one or more hydroxyl groups and one or more mercapto groups in a molecule.

2. An optical material formed of a poly(thio)urethane which is obtained by reacting the monomer mixture of claim 1.

3. The optical material of claim 2, wherein said n is 1 or 2.

4. The optical material of claim 2 or 3, wherein the compound having two or more mercapto groups in a molecule is a compound represented by general formula (II-a):

(II-a)

wherein p represents an integer of from 1 to 20.

5. The optical material of claim 2 or 3, said material being optically transparent.

6. An optical product formed of the optical material of claim 2 or 3.

7. The optical product of claim 6, said product being spectacle lenses.

* * * * *